US012788532B2

(12) United States Patent
Tripathi et al.

(10) Patent No.: US 12,788,532 B2
(45) **Date of Patent: *Nov. 10, 2026**

(54) REAL-TIME SURGICAL REFERENCE INDICIUM APPARATUS AND METHODS FOR SURGICAL APPLICATIONS

(71) Applicant: Alcon Inc., Fribourg (CH)

(72) Inventors: Ashok Burton Tripathi, Santa Barbara, CA (US); Michael A. Weissman, Santa Barbara, CA (US)

(73) Assignee: Alcon Inc., Fribourg (CH)

(*) Notice: Subject to any disclaimer, the term of this patent is extended or adjusted under 35 U.S.C. 154(b) by 0 days.

This patent is subject to a terminal disclaimer.

(21) Appl. No.: 18/536,516

(22) Filed: Dec. 12, 2023

(65) Prior Publication Data

US 2024/0099807 A1 Mar. 28, 2024

Related U.S. Application Data

(60) Continuation of application No. 17/563,548, filed on Dec. 28, 2021, now Pat. No. 11,872,091, which is a division of application No. 16/180,726, filed on Nov. 5, 2018, now Pat. No. 11,241,294, which is a continuation of application No. 13/024,948, filed on Feb. 10, 2011, now Pat. No. 10,117,721, which is a continuation-in-part of application No. 12/249,845, filed on Oct. 10, 2008, now Pat. No. 9,226,798.

(51) Int. Cl.
*A61B 90/00* (2016.01)
*A61B 34/00* (2016.01)
*A61F 2/00* (2006.01)
*A61F 2/12* (2006.01)
*A61F 9/007* (2006.01)

(52) U.S. Cl.
CPC .............. *A61B 90/37* (2016.02); *A61B 34/25* (2016.02); *A61B 90/39* (2016.02); *A61F 2/0059* (2013.01); *A61F 2/12* (2013.01); *A61F 9/007* (2013.01)

(58) Field of Classification Search
None
See application file for complete search history.

*Primary Examiner* — Michael J Carey
*Assistant Examiner* — Marjan Saboktakin
(74) *Attorney, Agent, or Firm* — Sanders IP Law

(57) ABSTRACT

Apparatus and methods are described which guide a surgeon in performing a reconstructive or cosmetic procedure. The apparatus and methods utilize three-dimensional presentations of the target surgical site incorporating one or more virtual surgical guides which help attain proper alignment and orientation of the post-surgical outcome.

26 Claims, 11 Drawing Sheets

REAL-TIME SURGICAL REFERENCE INDICIUM APPARATUS AND METHODS FOR SURGICAL APPLICATIONS

CROSS REFERENCE TO RELATED APPLICATIONS

This application is a continuation of U.S. patent application Ser. No. 17/563,548, which is a divisional of U.S. patent application Ser. No. 16/180,726 filed on Nov. 8, 2018 (issued as U.S. Pat. No. 11,241,294 on Feb. 8, 2022), which is a continuation of U.S. patent application Ser. No. 13/024,948 filed on Feb. 10, 2011 (issued as U.S. Pat. No. 10,117,721 on Nov. 6, 2018), which is a continuation-in-part of U.S. patent application Ser. No. 12/249,845 filed on Oct. 10, 2008 (issued as U.S. Pat. No. 9,226,798 on Jan. 5, 2016), the entire disclosure of which is incorporated herein by reference.

FIELD OF THE INVENTION

The present invention generally relates to the field of medical surgery, more particularly to medical surgical procedures utilizing visual imaging systems including open, unmagnified and magnified surgery utilizing visual imaging systems.

BACKGROUND

Medical surgery, whether reconstructive, cosmetic, palliative, or otherwise, is highly patient specific. Even though most surgery patients have the same basic physical architecture, every body has its own set of specific features and dimensions with respect to its individual organs, tissues, and structures that in certain cases may be significantly different from those of expected norms. As a result, surgeons must rely upon their individual experience and skills to adapt whatever surgical techniques they are practicing to the individual requirements as determined by each patient's unique structural features and dimensions.

To date, this individualized surgical adaptation has been accomplished essentially through freehand techniques based upon a pre-surgery examination and evaluation of the individual patient's target surgical site. This examination may include preliminary measurements as well as the surgeon making reference markings directly on the patient's skin with a pen or other form of dye or ink marking. Then, after the patient has been prepared and placed in position for surgery, typically in a supine or prone position as opposed to the often vertical positioning of the patient during the pre-surgery examination, the surgeon adapts the placement and configuration of initial surgical incisions to actual physical dimensions and circumstances found on or within the patient as the surgical procedure progresses. As a result, many initial measurements or reference markings on the patient's skin are at best general guides as to where to begin the procedure and have limited accuracy and influence on subsequent aspects of the procedure or on the overall outcome of the surgery.

Further complicating matters, there are numerous areas of the body which are not conducive to pre-surgery reference markings or measurements, such as fatty tissue that shifts substantially upon movement of the patient. For example, a marking placed on the breast of a female for cosmetic surgery when standing upright, will find a completely different position once the female assumes the supine position on the surgical table. This shift in pre-surgical markings is often a contributing factor to post operative asymmetry between cosmetically altered breasts.

Additionally, pre-surgical washing and sterilization processes may dissolve, alter or even remove reference markings from the patient's skin or other external tissues prior to the initiation of surgery. Similarly, subsequent wiping and contact with fluids, including the patient's body fluids, may remove or distort any remaining reference markings. As a result, even the most accurate surgical reference markings may lose any practical effectiveness beyond the initial stages of the surgical process.

Accordingly, in spite of ongoing development and growing sophistication of contemporary medical surgery, there is a continuing need in the art for the provision of effective virtual surgical guides.

SUMMARY

The present invention addresses the long-felt need for functional, useful, and effective surgical reference markings or guides by providing apparatus and associated methods for the generation of at least one accurate and effective, real-time, virtual surgical guide in conjunction with one or more real-time, multidimensional visualizations of a target surgical site, or at least a portion thereof, throughout a surgical procedure or any subpart thereof. In one embodiment, the multidimensional visualizations can be three dimensional (3D), stereoscopic, and high definition (HD). Moreover, in accordance with the teachings of the present invention, the virtual surgical guide or multiple guides are placed under the direct control, adjustment, and verification of the operating surgeon or surgical team. This control enables the operating surgeon or surgical team to fine tune a virtual surgical guide as desired or needed, and to align and lock it in place relative to an individual patient's target anatomy. Once so aligned, the virtual surgical guides function as effective templates or references for the surgeon or surgical team throughout the duration of an entire surgical procedure or any subpart thereof.

Moreover, aspects of the present invention make it possible for an operating surgeon to directly remove and reinstate one or more real-time, virtual surgical guide or guides as needed at any time throughout the duration of the surgical procedure at the control of and in response to the needs of the operating surgeon. Additionally, the present invention also makes it possible for the operating surgeon to replace at least one initial real-time, virtual surgical guide with one or more secondary or modified real-time, virtual surgical guides at an appropriate time during the surgical procedure to provide additional surgical guidance in real-time as desired or needed throughout the procedure.

Further still, the present invention also makes it possible for the operating surgeon to utilize multiple, different real-time, virtual surgical guides sequentially or simultaneously to achieve even more control over the surgical procedure or any subpart thereof.

As an added benefit, the at least one real-time, virtual surgical guides can be positioned accurately at an appropriate depth within the target surgical site to precisely indicate the correct reference position on or in tissue, tissues, or structures of interest. Further, the at least one real-time virtual surgical guide can be varied within the multidimensional visualization of the target surgical site as appropriate or desired during different phases of the surgical procedure where different tissues or structures are subsequently targeted or exposed. Additionally, the color, luminosity, transparency or visual characteristics of the at least one real-time, virtual surgical guide may be altered as appropriate or desired by the operating surgeon to enhance its contrast and visibility relative to the color and textures of the actual target surgical site of view and to provide notice or suggestion of impending dimensional or topographical objectives or restrictions upon the movement of a surgical instrument.

Exemplary apparatus and associated exemplary methods of the present invention accomplish these previously unobtainable benefits through the utilization of at least one real-time, multidimensional visualization module such as the TrueVision Systems, Inc. real-time 3D HD visualization systems as disclosed and claimed in the Applicant's co-pending patent applications made of reference herein. These exemplary multidimensional visualization modules function as either retrofit devices attached to existing stereomicroscopes in place of traditional microscope binocular optics or as a standalone stereoscopic 3D HD visualization apparatus. These exemplary apparatus can include various optical or electronic magnification systems including stereomicroscopes or can function as open surgery apparatus utilizing overhead cameras with or without magnification.

In conjunction with the multidimensional visualization module, the apparatus of the present invention includes at least one data processor such as a computer or microprocessor with appropriate software which, in accordance with the teachings of the present invention, is configured to produce or manage real-time, virtual surgical guides in conjunction with the real-time visualization of the target surgical site produced by the exemplary multidimensional visualization module. The data processor is provided with at least one user control input enabling the operating surgeon or surgical team to adjust all or at least portions of the pre-operative patient data, including for example a still image of the target surgical site, to verify and lock its alignment relative to the multidimensional visualization of the surgical site or to suit the needs or desires of the surgeon or surgical team before or during the surgical procedure involved.

In accordance with the teachings of the present invention, the at least one real-time, virtual surgical guide is generated or managed by the at least one data processor by utilizing pre-operative or intra-operative patient data. This patient data is used to manage, or in some cases generate the at least one real-time, virtual surgical guide. Exemplary data is generally in the form of one or more still images, preferably an HD still image, or a portion of a video clip, or alternatively, an HD photograph, all of which may be stereoscopic 3D.

Further, in accordance with the teachings of the present invention, the HD still image, photo or pre- or intra-operative patient data is reviewed or scanned to identify at least one specifically identifiable or distinguishing anatomical feature such as a scar or vascular pattern found within the target surgical site that is static or fixed with respect to the tissues or structures of interest in the surgical procedure. Additional fixed anatomical features can include matching body parts. For example, the matching body part is an opposite and symmetric body part that can be used as a surgical reference such as an ear, breast, tooth, nostril, arm, shoulder, leg, hand, ear or eye.

These fixed anatomical features are used to align and lock the HD still image or pre-operative patient data in place with the real-time multidimensional visualization of the target surgical site before and during the surgical process to avoid misalignment due to natural structural shifts within the target surgical site.

This initial alignment can be performed by the surgeon, the surgical team, the at least one data processor, or combinations thereof within the scope and teachings of the present invention. After the operating surgeon or surgical team verifies the placement of the virtual surgical guide, its position is finalized and locked into place by the operating surgeon prior to initiation of the surgical procedure or during the procedure as appropriate for the guide involved.

In further accordance with the teachings of the present invention, the HD still image now aligned and locked with the real-time multidimensional visualization of the target surgical site is modified to include at least one virtual surgical guide which is uniquely suited for the surgical procedure and the specific patient's target anatomy. The guide can be provided either before or after locking the still image in alignment with the multidimensional visualization. In other words, virtual surgical guides can be added to the still image directly. This modification is accomplished by the at least one data processor or, alternatively by an additional dedicated processor for generating the surgical guide or multiple guides, or by combinations thereof as determined by the surgeon or surgical team. Once incorporated into position, the at least one real-time, virtual surgical guides function as a reference or indicia to assist the surgeon performing the relevant portion of a surgical procedure in spite of the possibility that the target surgical site may have moved or re-oriented relative to other patient physical features or structures after the HD still image or pre-operative patient data is captured or obtained.

It should be noted that the real-time, virtual surgical guides described can be presented as 2D or 3D guides as appropriate or desired within the scope and teaching of the present invention. For example, a virtual surgical guide intended to direct a surgical incision of relatively flat tissue can be presented as a two dimensional line incorporated into the multidimensional or 3D visualization provided by the visualization module. Similarly, surgeons may prefer 3D guides when operating on more complex shapes and surfaces.

Further, the apparatus and methods of the present invention are ultimately under the control of the operating surgeon. In some embodiments, the apparatus and associated methods can be fully automated to assist the surgeon or surgical team; however, the ultimate control of the process resides with the operating surgeon.

Though the methods and apparatus of the present invention can be applicable to any form of surgery, such as ophthalmologic surgery, neurosurgery, orthopedic surgery, or on any target structure or tissue, the features and advantages of the present invention are most readily understood when presented in the non-limiting context of reconstructive and cosmetic surgeries.

Further advantages and features of the apparatus and methods of the present invention will be provided to those skilled in the art from a consideration of the following Detailed Description taken in conjunction with the associated Figures, which will first be described briefly.

DETAILED DESCRIPTION

Figure 1:
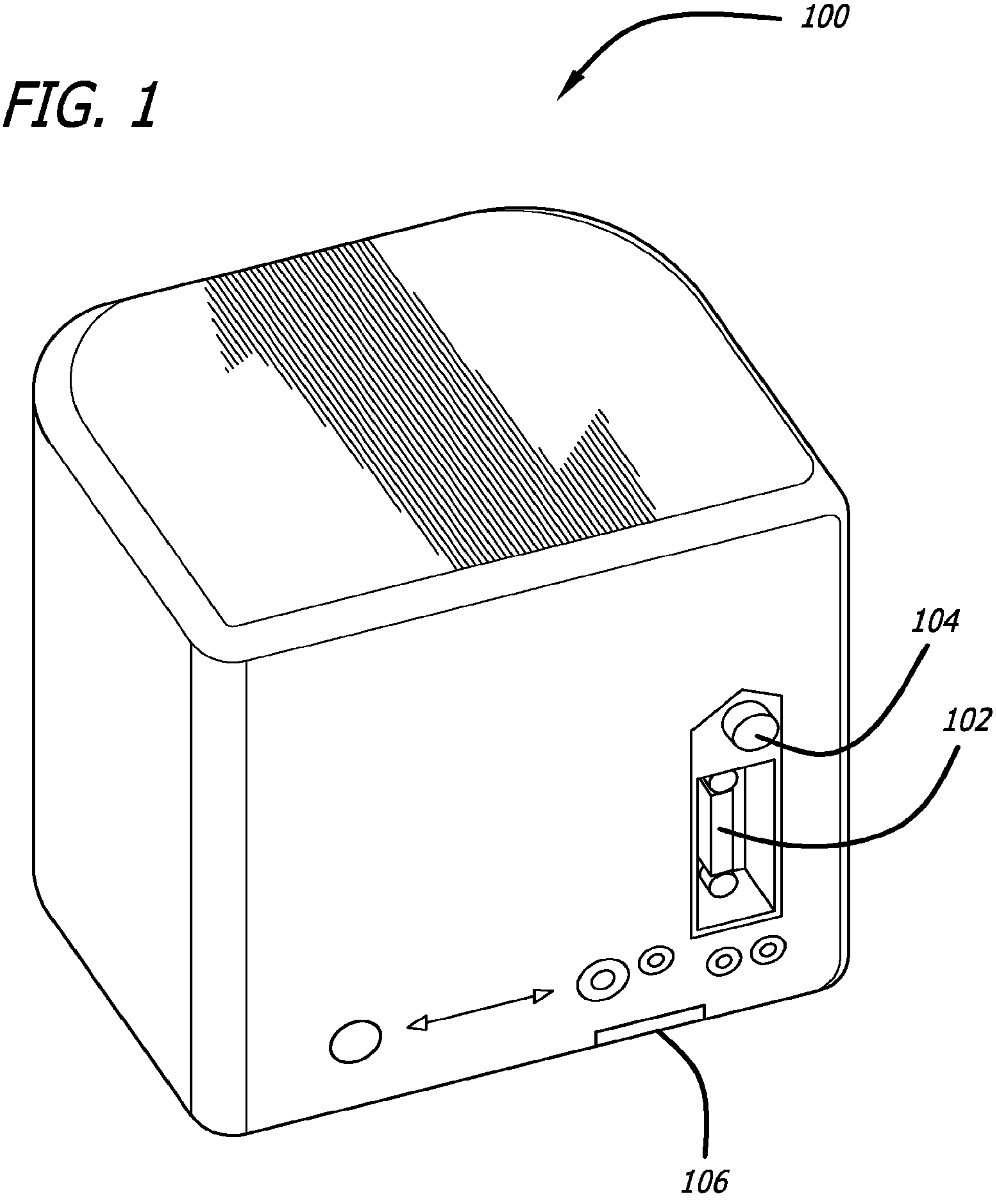
FIG. 1 is an illustration of an exemplary image capture module of the present description.

Described herein are apparatus and methods for the generation and management of one or more accurate, real-time, virtual surgical guide or multiple virtual surgical guides in conjunction with at least one real-time, multidimensional visualization of at least a portion of a target surgical site throughout a surgical procedure or any subpart thereof. In some embodiments, the multidimensional visualization is stereoscopic three-dimensional (3D) video and also may be in high definition (HD). Those skilled in the art will appreciate that a 3D HD real-time visualization will be most effective in enabling a physician to perform a medical or surgical procedure. Moreover, the virtual surgical guides can be placed under the direct control and adjustment of the operating surgeon or surgical team, thereby enabling the surgeon to have tight control over the guides and align them properly with one or more fixed anatomical features. Once the surgeon has aligned the virtual surgical guides, they can be locked in place and act as effective guides for the surgeon throughout any or all portions of a surgical procedure at the discretion and control of the surgeon or surgical team.

In a broad aspect, an exemplary apparatus of the present invention incorporates three primary elements: one or more real-time multidimensional visualization modules, one or more data processors, and one or more user control inputs. The three elements can be physically combined into a single device or can be linked as physically separate elements within the scope and teachings of the present invention as required by the specific surgical procedure being practiced.

Exemplary apparatus suitable for practicing the present methods incorporate the basic structural components of the Applicant's TrueVision Systems, Inc. real-time 3D HD visualization systems described in the Applicant's co-pending U.S. applications: Ser. No. 11/256,497 entitled "Stereoscopic Image Acquisition Device," filed Oct. 21, 2005; Ser. No. 11/668,400 entitled "Stereoscopic Electronic Microscope Workstation," filed Jan. 29, 2007; Ser. No. 11/668,420 entitled "Stereoscopic Electronic Microscope Workstation," filed Jan. 29, 2007; Ser. No. 11/739,042 entitled "Stereoscopic Display Cart and System," filed Apr. 23, 2007; and Ser. No. 61/042,606, entitled "Apparatus and Methods for Performing Enhanced Visually Directed Procedures Under Low Ambient Light Conditions," filed Apr. 4, 2008; Ser. No. 12/249,845 entitled "Real-time Surgical Reference Guide Apparatus and Methods for Surgical Application," filed Oct. 10, 2008; Ser. No. 12/828,074 entitled "Systems, Apparatus and Methods for Digital Image Capture with Variable Density Display and High Resolution Electronic Zoom," filed Jun. 30, 2010, all of which are fully incorporated herein by reference as if part of this specification.

The multidimensional visualization module is used to provide a surgeon with a real-time visualization of at least a portion of a target surgical field, which can be any part of the body of a human or mammalian subject or patient.

"Real-time" as used herein generally refers to the updating of information at essentially the same rate as the data is received. More specifically, "real-time" is intended to mean that the image data is acquired, processed, and transmitted from the photosensor of the visualization module at a high enough data rate and at a low enough time delay that when the data is displayed, objects presented in the visualization move smoothly without user-noticeable judder, latency or lag. Typically, this occurs when new images are acquired, processed, and transmitted at a rate of at least about 25 frames per second (fps) and displayed at a rate of at least about 50 fps and when the combined processing of the video signal has no more than about $1/10^{th}$ second of delay.

In other embodiments according to the present invention, new images are acquired, processed, and transmitted at a rate of at least about 30 fps, about 35 fps, about 40 fps, about 50 fps, about 60 fps, about 70 fps, about 80 fps, about 90 fps or about 120 fps. Also, new images are displayed at a rate of at least about 60 fps, about 70 fps, about 80 fps, about 90 fps or about 120 fps. The signal processing can have no more than about $1120^{th}$ second of delay, about $1130^{th}$ second of delay, about $1150^{th}$ second of delay, about $1190^{th}$ second of delay, about $11120^{th}$ second of delay, about $11500^{th}$ second of delay, or about $111000^{th}$ second delay or more.

It should be appreciated that while it is preferred to utilize a multidimensional visualization module that provides a surgeon with a real-time 3D visualization of at least a portion of the target surgical field, it is contemplated as being within the scope of the present disclosure for the visualization module to provide a real-time visualization that is a real-time 2-dimensional (2D) visualization. However, the use of a 3D visualization is preferred as it provides many benefits to the surgeon including more effective visualization and depth of field. In one embodiment, the visualization of the target surgical field is in HD.

The term "high definition" or "HD" as used herein can encompass a video signal having a resolution of at least 960 lines by 720 lines and to generally have a higher resolution than a standard definition (SD) video. For purposes of the present invention, this can be accomplished with display resolutions of 1280 lines by 720 lines (720p and 720i) or 1920 lines by 1080 lines (1080p or 1080i). In contrast, standard definition (SD) video typically has a resolution of 640 lines by 480 lines (480i or 480p) or less. It is however, within the scope of the present invention that the multidimensional visualization can be in SD, though HD is preferred.

The apparatus described herein can be embodied in a single device which can be retrofitted onto existing surgical equipment such as surgical microscopes or open surgery apparatus. This is highly advantageous as the retrofit embodiments can be added to existing systems, allowing expensive equipment to simply be upgraded as opposed to purchasing an entirely new system. At the same time, a standalone device allows one to practice the features of the present invention without an arsenal of pre-owned equipment. The exemplary apparatus can include various optical or electronic magnification systems including stereomicroscopes or can function as open surgery apparatus utilizing cameras and overhead visualizations with or without magnification.

FIG. 1 illustrates image capture module 100 which includes a multidimensional visualization module and an image processing unit, both housed within image capture module 100, and therefore, not depicted. The exemplary image capture module comprises at least one photosensor to capture still images, photographs or videos. As those skilled in the art will appreciate, a photosensor is an electromagnetic device that responds to light and produces or converts light energy into an electrical signal which can be transmitted to a receiver for signal processing or other operations and ultimately read by an instrument or an observer. Communication with image capture module 100 including control thereof and display output from image capture module 100 are provided at first connector 102. Image capture module power is provided by a lead secured to second connector 104. Additionally, image capture module 100 can manually control the transmitted light intensity using iris slider switch 106.

Figure 2:
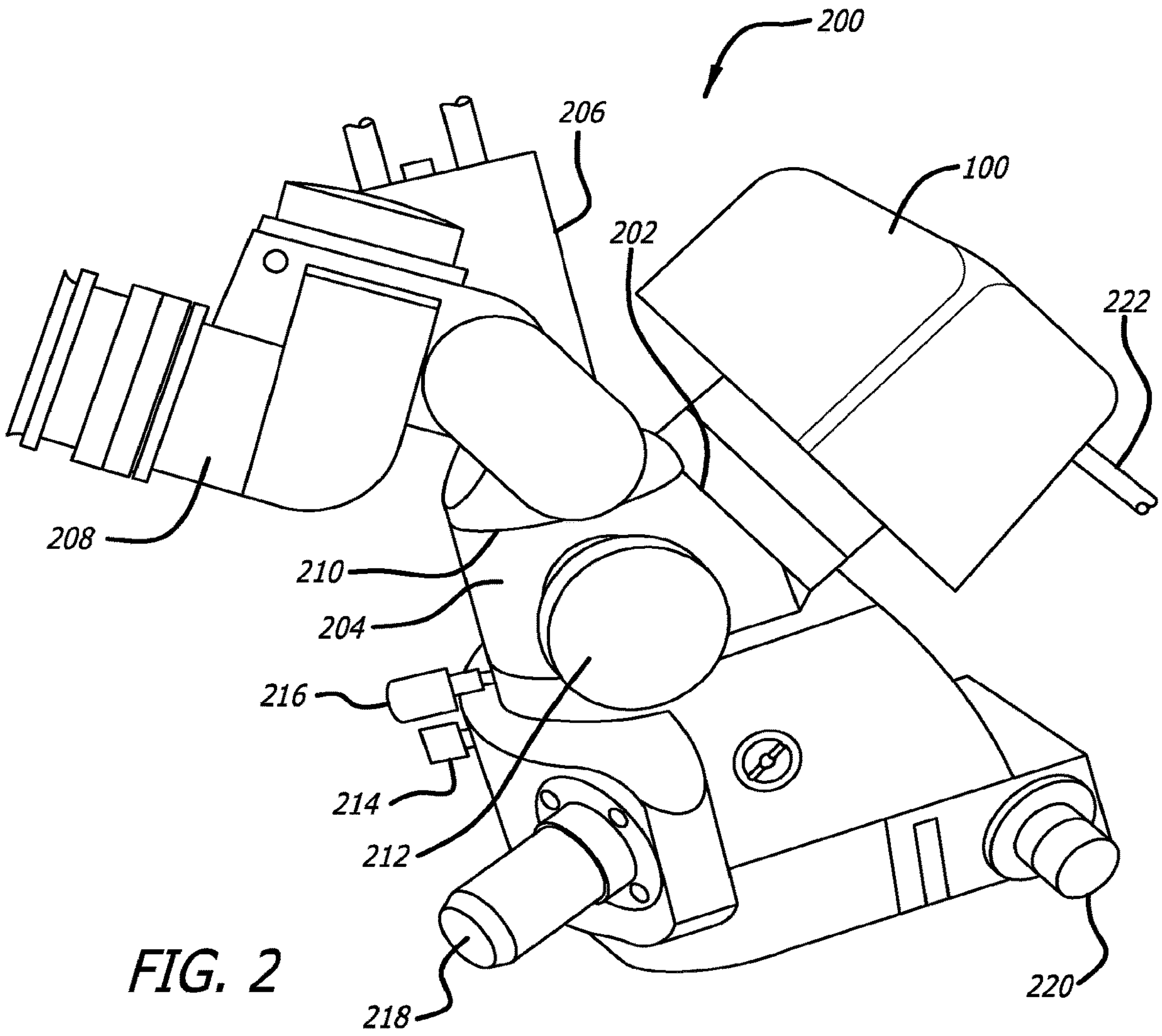
FIG. 2 is an illustration of an exemplary apparatus of the present description retrofitted on a surgical microscope.

In another embodiment, FIG. 2 illustrates retrofitted surgical microscope 200 incorporating image capture module 100 retrofitted onto surgical microscope 200. Surgical microscope 200 is retrofitted with image capture module 100 coupled to first ocular port 202 on ocular bridge 204. Further, ocular bridge 204 couples video camera 206 to a second ocular port (not shown) and binocular eyepiece 208 to third ocular port 210. Optional forth ocular port 212 is available for further retrofits to surgical microscope 200. Although surgical microscope 200 has been retrofitted with image capture module 100, it still retains the use of conventional controls and features such as, but not limited to, iris adjustment knob 214, first adjustment knob 216, second adjustment knob 218, illumination control knob 220, and an objective lens (not shown). Further still, image capture module 100 can send and receive information through signal cable 222.

Figure 3:
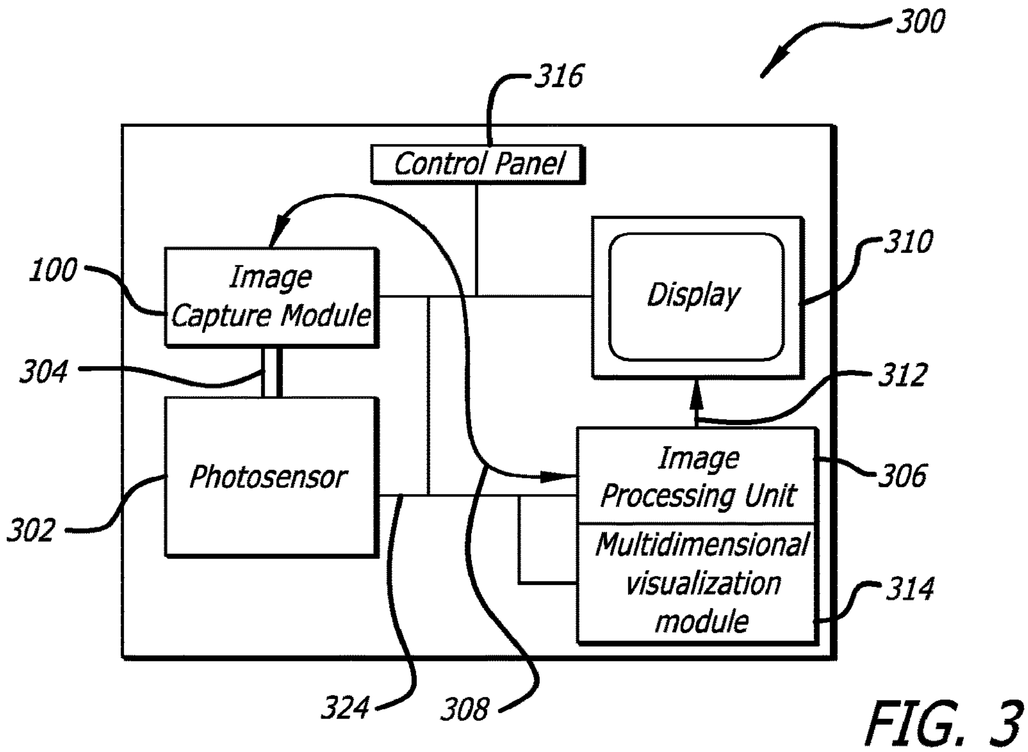
FIG. 3 is a schematic overview of an exemplary embodiment of an apparatus of the present description illustrating features thereof.

An exemplary, non-limiting configuration of components is illustrated in FIG. 3. Apparatus setup 300 includes image capture module 100, coupled to photosensor 302 by bi-directional link 304. Those skilled in the art will appreciate that bi-directional link 304 can be eliminated where image capture module 100 and photosensor 302 are physically the same device. Image capture module 100 is in direct communication with image processing unit 306 by first cable 308. First cable 308 can be a cable connecting two physically different devices, can be a cable connecting two physically different components within the same device, or can be eliminated if image capture module 100 and image processing unit 306 are physically the same device. First cable 308 allows, in certain embodiments, bi-directional communication between image capture module 100 and image processing unit 306. Image processing unit 306 generates images and videos that are presented on display 310. It is within the scope of the present description that display 310 include multiple displays or display systems (e.g. projection displays). An electrical signal (e.g. video signal) is transmitted from image processing unit 306 to display 310 by a second cable 312, which is any kind of electrical signal cable commonly known in the art. Image processing unit 306 can be in direct communication with multidimensional visualization module 314, which can also send electrical signals to display 310 via second cable 312. In one embodiment, image capture module 100, image processing unit 306, and multidimensional visualization module 314 are all housed in a single device or are physically one single device. Further, one or all of the components of the present invention can be manipulated by control panel 316 via cable network 318. In one embodiment, control panel 316 is wireless.

"Display," as used herein, can refer to any device capable of displaying a still or video image. Preferably, the displays of the present disclosure display HD still images and video images or videos which provide a surgeon with a greater level of detail than an SD signal. More preferably, the displays present such HD stills and video images in 3D. Exemplary displays include HD monitors, cathode ray tubes, projection screens, liquid crystal displays, organic light emitting diode displays, plasma display panels, light emitting diodes, 3D equivalents thereof, and the like. In some embodiments, 3D HD holographic display systems are considered to be within the scope of the present disclosure. In one embodiment, display 310 is a projection cart display system and incorporates the basic structural components of Applicant's TrueVision Systems, Inc. stereoscopic image display cart described in Applicant's co-pending U.S. application: Ser. No. 11/739,042, entitled "Stereoscopic Display Cart and System" filed Apr. 23, 2007, which is fully incorporated herein by reference as if part of this specification.

The exemplary image processing units as illustrated in FIGS. 1, 2 and 3 include a microprocessor, e.g. a data processor, or computer configured to process data sent as electrical signals from image capture module 100 and to send the resulting processed information to display 310, which can include one or more visual displays for observation by a physician, surgeon or a surgical team. Image processing unit 306 may include control panel 316 having user operated controls that allow a surgeon to adjust the characteristics of the data from image capture module 100 such as the color, luminosity, contrast, brightness, or the like sent to the display.

In one embodiment, image capture module 100 includes a photosensor, such as a camera, capable of capturing a still image or video images, preferably in 3D and HD. It is within the teachings herein that the photosensor is capable of responding to any or all of the wavelengths of light that form the electromagnetic spectrum. Alternatively, the photosensor may be sensitive to a more restricted range of wavelengths including at least one wavelength of light outside of the wavelengths of visible light. "Visible light," as used herein, refers to light having wavelengths corresponding to the visible spectrum, which is that portion of the electromagnetic spectrum where the light has a wavelength ranging from about 380 nanometers (nm) to about 750 nm.

More specifically, the one or more data processors are also in direct communication with multidimensional visualization module 314 and/or image capture module 100. The data processors, in their basic form, are configured to produce one or more real-time virtual surgical guides in conjunction with the real-time visualization of at least a portion of the target surgical site produced by multidimensional visualization module 314. In another configuration, the surgeon can manually input virtual surgical guides as he sees fit, and in this case, the at least one data processor implements the guide into the real-time visualization and manages its location thereafter. In one embodiment, the data processor or processors are incorporated into multidimensional visualization module 314. In another embodiment, at least one data processor is a standalone processor such as a workstation, personal data assistant or the like interacting and controlling image capture module 100.

The one or more data processors are controlled by built-in firmware upgradeable software and at least one user control input, which is in direct communication with the data processors. The at least one user control input can be in the form of a keyboard, mouse, joystick, touch screen device, remote control, voice activated device, voice command device, camera (e.g., for gesture, position, or movement recognition) or the like and allows the surgeon to have direct control over the one or more virtual surgical guides. In one exemplary embodiment, user input is controlled by a mouse pointer which is interactive with the display.

Figure 4:
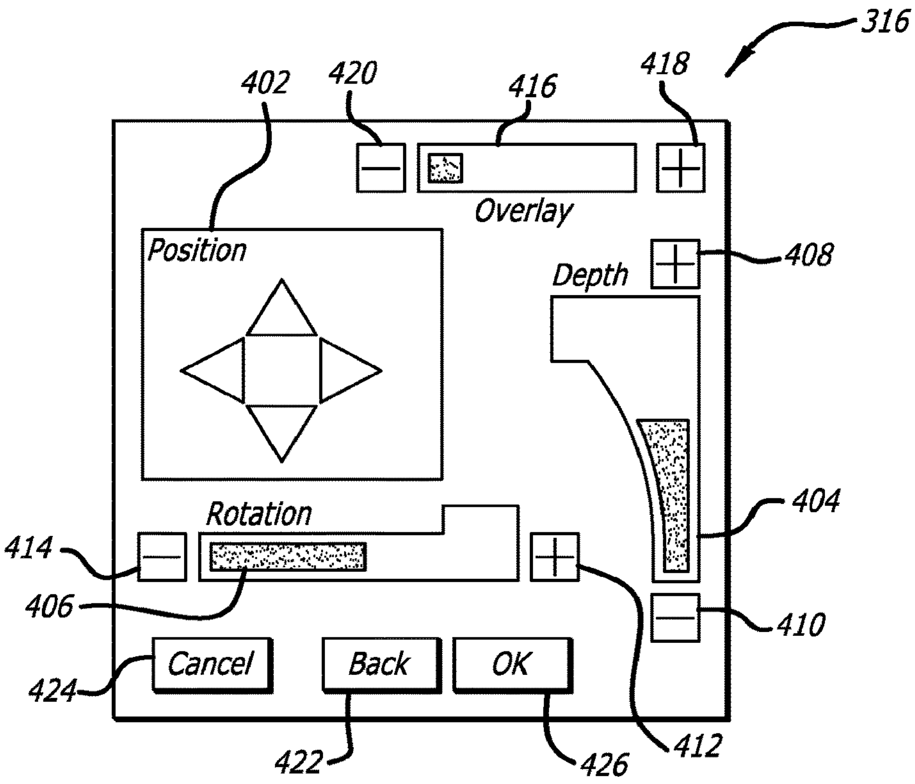
FIG. 4 is a plan view of an exemplary alignment control panel of the present description illustrating an exemplary embodiment of user input control thereof.

FIG. 4 illustrates an exemplary user control input, in the form of control panel 316. Control panel 316 includes multidirectional navigation pad 402 with user inputs allowing a controlling surgeon or operator to move data vertically, horizontally or any combination of the two. Additionally, the depth of the data can be adjusted using depth rocker 404 of control panel 316 and the rotation can be adjusted using rotation rocker 406 of control panel 316. Depth can be adjusted using both increase depth position 408 and decrease depth position 410 of depth rocker 404. Additionally, rotation can be adjusted using both increase rotation position 412 and decrease rotation position 414 of rotation rocker 406. Other non-limiting adjustments that can be made to the pre-operative image or to the real-time visualization include changes in diameter, opacity, color, horizontal and vertical size, and the like, as known in the art. Further, overlay can be adjusted using overlay rocker button 416. Overlay rocker button 416 is used to pan in and out of an overlay locked within the real-time multidimensional visualization, for example, a still image overlaid thereon. The overlay can be made more intense using intensity button 418 or less intense using visualization button 420.

It should be noted that in exemplary control panel 316 an adjustment can be undone by the surgeon utilizing "back" button 422. Further, the entire process can be ended by the surgeon by engaging "cancel" button 424. Further, once the surgeon is satisfied with the alignment of the data, the alignment is locked into place by engaging "ok" button 426.

Alternative control panel embodiments for the manipulation and alignment of the pre-operative still image are contemplated as being within the scope and teachings of the present description. For example, a hand-held device such as a 3D mouse can be used as known in the art to directly position templates, images, and references within the real-time multidimensional visualization. Such devices can be placed on a tabletop or held in mid-air while operating. In another embodiment, foot switches or levers are used for these and similar purposes. Such alternative control devices allow a surgeon to manipulate the pre-operative still image without taking his or her eyes off of the visualization of a surgical procedure, enhancing performance and safety.

In yet another alternative embodiment, a voice activated control system is used in place of, or in conjunction with, control panel 316. Voice activation allows a surgeon to control the modification and alignment of the pre-operative still image and its associated guides as if he was talking to an assistant or a member of the surgical team. As those skilled in the art will appreciate, voice activated controls typically require a microphone and, optionally, a second data processor or software to interpret the oral voice commands. In yet a further alternative embodiment, a system is envisioned wherein the apparatus utilizes gesture commands to control pre-operative image adjustments. Typically, as known in the art, the use of gesture commands involves an apparatus (not shown) having a camera to monitor and track the gestures of the controlling physician and, optionally, a second data processor or software to interpret the commands.

Apparatus setup 300 can be used in many medical settings in many different examination room/operating room combinations. For example, apparatus setup 300 can be used in an examination room during a particular surgical procedure. Image capture module 100 can be coupled or mounted to any piece of medical equipment that is used in an examination room setting wherein pre-operative data can be captured. Apparatus setup 300 can also be used in an operating room. Therein, image capture module 100 is used to capture a real-time visualization of at least a portion of the target surgical site, preferably in HD, more preferably in 3D.

Apparatus setup 300 used in an examination room can be in direct communication with another apparatus setup 300 in the operating room, or conversely the same setup can be moved and used in the operating room. The two apparatus setups can be directly connected by cable, or indirectly connected through an intermediary device such as a computer server. In some embodiments, the two setups can be separate systems, even in different physical locations. Data can be transferred between the two systems by any means known to those skilled in the art such as an optical disc, a flash memory device, a solid state disk drive, a wired network connection, a wireless network connection or the like.

A further understanding of the present disclosure will be provided to those skilled in the art from an analysis of exemplary steps utilizing the apparatus described above to practice the associated methods disclosed herein.

Though the apparatus and associated methods are applicable to any type of surgery on any target structure or tissue, the exemplary features and advantages will be disclosed in the illustrative, but non-limiting context of reconstructive and cosmetic surgeries. These types of surgical procedures are quite common, and their popularity has grown over time. For example, there are over 1.2 million of the five most common types of cosmetic surgeries (breast augmentation, lipoplasty, eyelid surgery, rhinoplasty, and abdominoplasty) performed per year in the United States. Non-surgical methods, for example botulinum toxin injection, which can also utilize the apparatus and methods described herein, account for 2.5 million procedures per year alone.

Cosmetic surgery as described herein can include highly invasive to minimally invasive to noninvasive cosmetic surgical procedures. For example, a highly invasive cosmetic procedure might include a facelift. More moderate cosmetic surgeries include cheek and breast implants and lipoplasty wherein a smaller incision is used and less post surgery trauma is involved. Minimally invasive cosmetic procedures might include botulinum toxin injections or dermal filler injections. Non-invasive cosmetic procedures can include transdermal treatments, heat treatments, UV treatments and the like.

Reconstructive surgeries as described herein can be both inclusive with cosmetic surgery and exclusive. Reconstructive surgery can be as simple as fixing a broken nose, repairing a broken finger, or reconstructing a defect to an ear.

On the other hand, reconstructive surgery can be far more elaborate, for example, reconstructing the skin of a third degree facial burn victim or a victim of a severe birth defect such as a cleft pallet.

For the sake of brevity, each and every cosmetic and reconstructive surgery will not be listed. Rather, one skilled in the art will readily understand that virtually any procedure can utilize at least a portion of the apparatus and methods described herein. And, although different types of procedures vary greatly in complexity, skill needed, pain endured, recovery period, post-surgery trauma and the like, all procedures rely on the satisfaction of the patient with the ultimate result. The apparatus and methods described herein enhance the outcome of the particular procedure and hence the satisfaction of the patient. The surgery location can be one selected from the group consisting of a nose, one or more eye, one or more cheek, a forehead, one or more ear, one or more breast, an abdomen, one or more hand, one or more foot, one or more leg, one or more tooth, and combinations thereof.

One of the many advantages of the apparatus and methods according to the present invention is that symmetric or opposite anatomical features can be tailored to match following surgery. For example, utilizing the teachings of the present invention, matching sets of generally symmetrical features can be produced including ears, breasts, teeth, nostrils, arms, shoulders, legs, hands, ears, eyes and the like. In an exemplary embodiment, one breast can be the template for the opposite breast, so that after surgery, the two breasts match in size and shape.

With an understanding of the contemporary need for accurate and precise cosmetic surgery and reconstruction of tissues, the following non-limiting, exemplary embodiments illustrate the previously unobtainable features and advantages of the apparatus and methods of the present invention with relation to providing at least one accurate, real-time virtual surgical guide oriented with at least one fixed anatomical feature that can accurately and precisely guide a surgeon in performing a cosmetic or reconstructive procedure on a patient or subject.

As a first step in cosmetic procedure, for example a face lift, according to the present description, a pre-operative or intra-operative data set is captured, produced, or obtained. The data set, either pre-operative or intra-operative, can include any portion of data about a patient including, for example, the patient's weight, age, hair color, bodily features, medical history, and at least one image of at least a portion of the patient's target surgical anatomy, for example the face and the like.

In an exemplary embodiment, the dataset includes a still image of at least a portion of the ocular and forehead region of the patient undergoing the procedure. In some embodiments, the still image is in HD. A data set can also include a mark-up of the patients target surgical site for analysis, measurement, or alignment as well as topographical data or measurements.

It is also within the scope of the present invention that the still image can be captured during the surgical procedure or just prior to the surgical procedure when the patient is in the operating room. Surgeons can capture still images on the fly as the procedure is progressing. For example, a pre-operative still image can be captured and subsequent still images can be captured and processed as described herein as needed by the surgeon. Therefore, as used herein, the term "still image" can comprise both pre-operative still images and intra-operative still images. In some cases, it is more preferable to simply capture a still image intra-operatively to save time, for example, in a traumatic situation.

Although it is preferable that the still image be captured using an image capture module as described herein, the still image need not be captured using the apparatus described herein. Rather, a digital camera, preferably an HD digital camera can be used to capture the preoperative still image. This image can be uploaded into the image capture module and processed by the at least one data processor.

Figure 5:
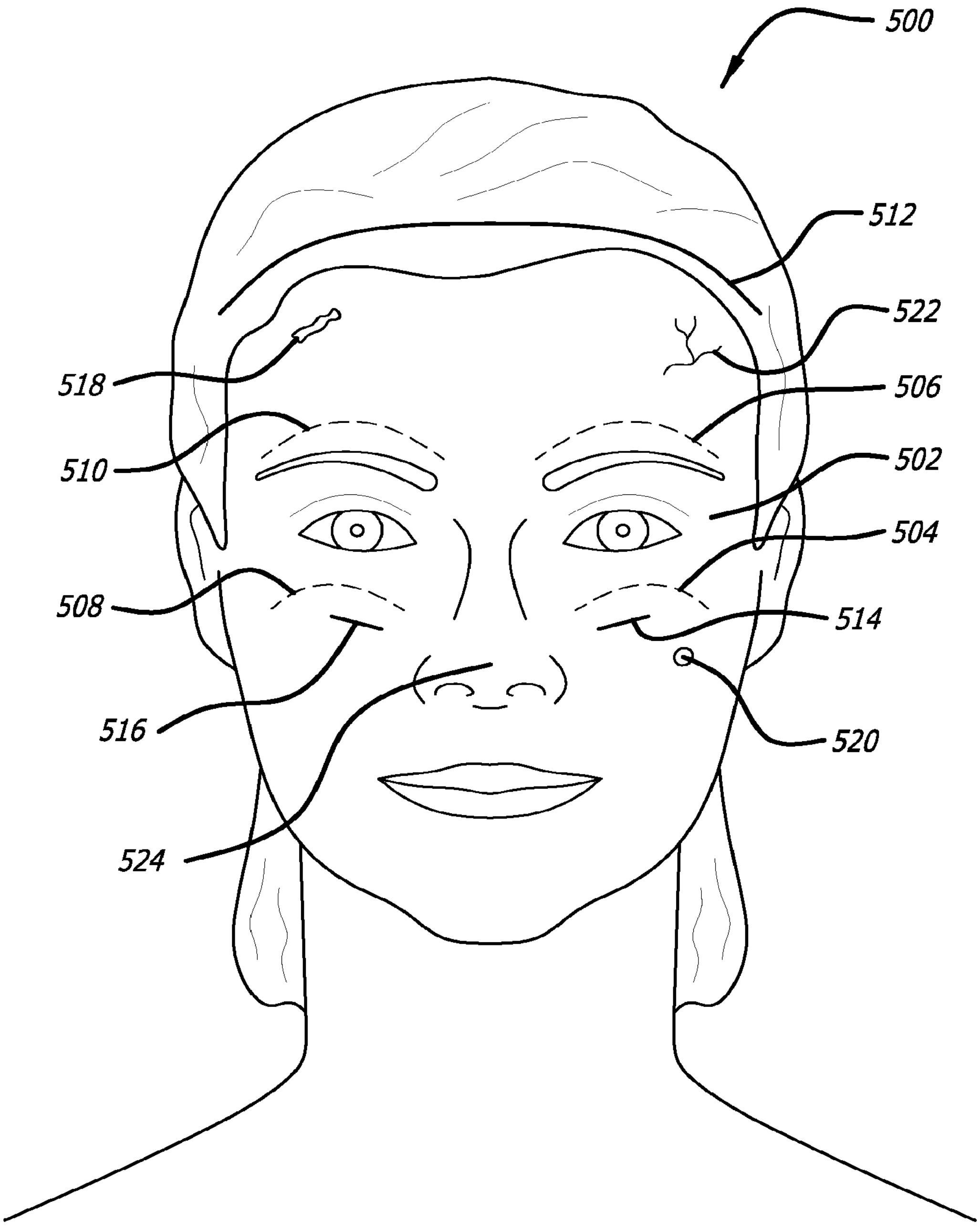
FIG. 5 is an illustration of a pre-operative still image including virtual surgical guides and fixed anatomical features.

As illustrated in FIG. 5, once the still image is captured, whether that be pre- or intra-operatively, the surgeon can add one or more virtual surgical guides in the form of templates or freehand markings. For example, still image 500 including facial region 502, includes a first set of guides, sub eye guide 504 and above eye guide 506 can be drawn freehand by the surgeon. Conversely, a template can be used to draw these guidelines based on a predetermined algorithm or framework.

At this point, because symmetry between the right and left regions of the face are generally desired, the at least one data processor can calculate and draw complementary second sub eye guide 508 and second above eye guide 510 that symmetrically match the existing guides. On the other hand, a surgeon may draw second sub eye guide 508 and second above eye guide 510 freehand.

Further still, markings representing the incisions to be made by the surgeon can be added to the still image. For example, cut guide 512 can be added to the scalp region. Further, first virtual cheek guide 514 and second virtual cheek guide 516 can be added to the still image by the surgeon. First virtual cheek guide 514 and second virtual cheek guide 516 are interesting additions because they are incisions to be made on the interior of the patients mouth, i.e. on interior tissues where physical markings are not practical or functional.

Further, as mentioned above, axis guides can be added to the still image as templates. For example, in FIG. 6, eye brow axis 602, eye axis 604, lip axis 606 and forehead axis 608 are all used to orient facial features with proper vertical symmetry. All four axes can be generated and placed by the at least one data processor and moved and scaled by the surgeon as needed.

Figure 6:
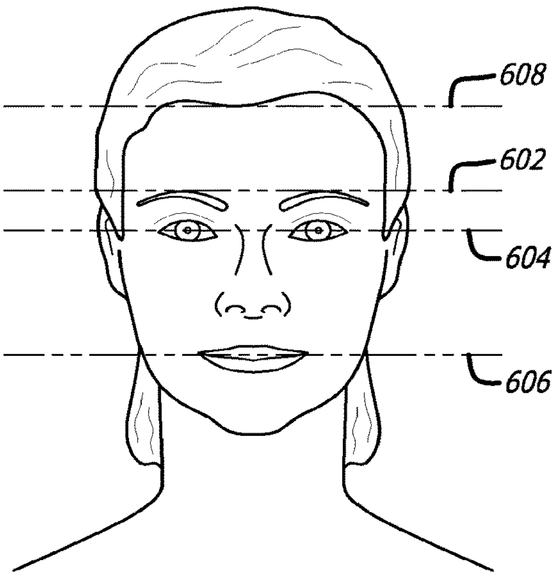
FIG. 6 is an illustration of exemplary virtual surgical guides.
Figure 7:
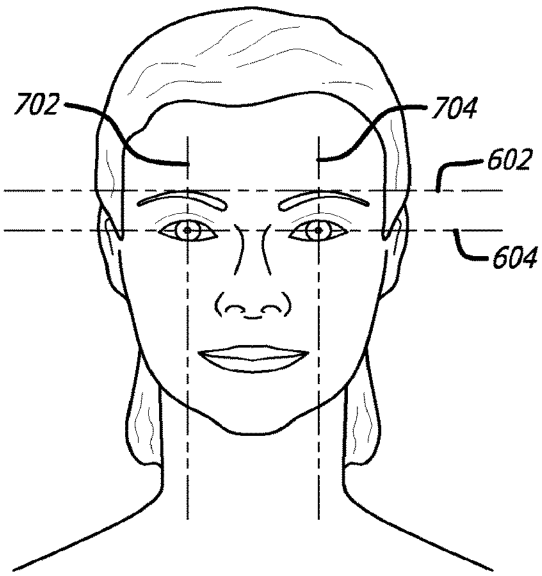
FIG. 7 is an illustration of additional exemplary virtual surgical guides.

An alternate configuration of guide templates is illustrated in FIG. 7. Here, both eye brow axis 602 and eye axis 604 are used with first vertical axis 702 and second vertical axis 704. The addition of first vertical axis 702 and second vertical axis 704 allow the surgeon to properly align facial features with horizontal symmetry in addition to just vertical symmetry as illustrated in FIG. 6.

Figure 8:
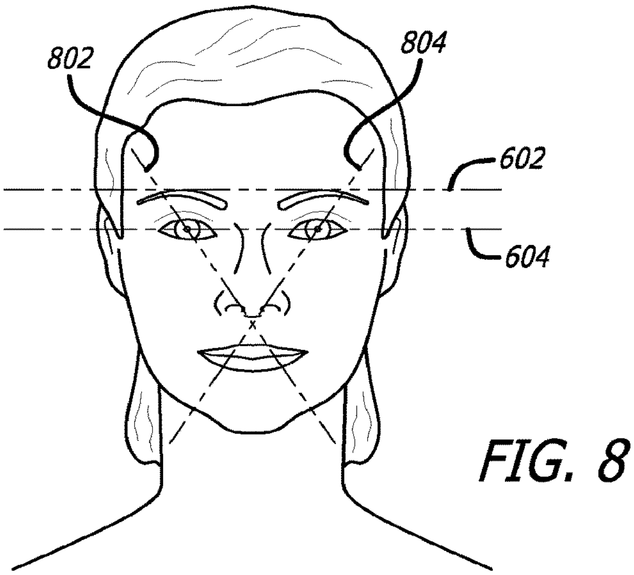
FIG. 8 is an illustration of further exemplary virtual surgical guides.

Further, another alternate configuration of the guide templates of the present invention is illustrated in FIG. 8. Here, both eye brow axis 602 and eye axis 604 are again used, but now with first cross axis 802 and second cross axis 804. The addition of first cross axis 802 and second cross axis 804 allow the surgeon to properly align facial features with horizontal symmetry in general and relative to each other as well as in relation to the center point of the nose. This is in addition to the vertical symmetry illustrated in FIG. 6 or the vertical and horizontal symmetry illustrated in FIG. 7.

At this point in the surgical procedure, the surgeon can decide which virtual guides are to be static and which are to be dynamic. In other words, cut guide 512 will likely be a static guide because as the patient's head is moved during surgery, this guide line should track the movement. Conversely, first above eye guide 506 and second above eye guide 510 will likely be dynamic because as the facial features are lifted, these guides mark the final position of, for example, the eyebrow line and need to be fixed dynamically in relation to the lift of the facial features.

Prior to the present description, it was the individual and variable skill of the surgeon compensating for these natural physical differences between measured pre-surgical markings and variations during the surgical procedure that determined the degree of post-operative success of the procedures involved and the resultant degree of patient satisfaction with the procedure.

In another embodiment of the present invention, pre-surgical markups can be physically applied to the patient's tissues, e.g. with a pen, after which time a still image is captured. This still image is analyzed by the at least one data processor to identify at least one fixed anatomical feature. At the same time, prior to, or subsequent to this identification, the at least one data processor can identify the pre-surgical markings on the patient's tissues and add them to the still image as virtual surgical guides for use during the surgery. In one exemplary embodiment, the pen used by the surgeon to apply the pre-surgical markings includes an ink that is specifically identifiable to the at least one data processor. This specifically identifiable ink can be, for example, fluorescent or infrared.

In a second step, the pre-operative data set still image, or just the still image, captured in the first step, with or without virtual surgical guides, is matched to a real-time multidimensional visualization of at least a portion of the target surgical site. Matching the still image to the multidimensional visualization is important because the target surgical site may have changed subsequent to the pre-operative image still being captured such as by tissue shifting and rotating when the patient changes positions. As a result, the measurements obtained during the pre-operative examination may no longer be accurate or easily aligned in light of such changes in the patient's physical alignment and position. Additionally, any surgical markings that may have been applied to the patient's tissues during the pre-operative examination may have shifted, been wiped away, or blurred.

At this point, the pre-operative still image of the patient or the target surgical site on the patient is analyzed by a surgeon, a surgical team or the at least one data processor of the apparatus to identify at least one distinct, visible anatomical feature that is static, or fixed, and recognizable relative to and within the target surgical field. Utilizing the teachings described herein, this at least one fixed anatomical feature is used to align or register the still image with the real-time multidimensional visualization of the target surgical site during the actual surgery.

During processing of the still image by the at least one processor, the software locates at least one fixed anatomical feature within the region of the surgical site. The at least one fixed anatomical feature is selected from the group consisting of vasculature, vascular networks, vascular branching patterns, moles, scratches, hairs, hairlines, dimples in the skin, skin blemishes, skin wrinkles, skin folds, skin protrusions, skin deformities, skin blotches, scars, bony processes, bony ridges, bony features, and combinations thereof. For example, as illustrated in FIG. 5, still image 500 includes facial region 502 including scar 518, mole 520, vasculature 522, nose protrusion 524 and the like which are identified by the at least one processor and accompanying software.

In one embodiment, once at least one fixed anatomical feature has been identified in the pre-operative patient data still image, the still image and the associated fixed anatomical feature or features are stored for later processing and use in the operating room. It should be noted that the pre-operative patient data need not be taken in a separate operation or at a separate location from the operating room or theater. For example, during surgery to reconstruct a traumatic injury, the entire process can be performed in the operating room to save time.

In another embodiment, the pre-operative data can be captured during the procedure itself or intra-operatively. When capturing data during a procedure, it is possible to then present a mirror image of an anatomical feature on the opposite anatomical feature to act as a guide. With the goal of achieving symmetry, the reference anatomy will sometimes need to be inverted to a mirror image so that it can be aligned with the multidimensional visualization of the mirrored anatomical feature. For example, during traumatic ear reconstruction, instead of using the pre-operative patient data still image, a surgeon can use a mirror image presentation of the undamaged ear taken during the surgery itself.

A third step involves the surgeon, the surgical team, the at least one data processor, or a combination thereof aligning the pre-operative still image of the target surgical site with the real-time multidimensional visualization of the target surgical site. Generally speaking, this alignment is accomplished utilizing specific fixed anatomical features identified within the pre-operative still image of the target surgical site to align the still image with the real-time multidimensional visualization of the target surgical field. This allows the pre-operative still image to be aligned accurately with the tissues of the target surgical site regardless of whether the target surgical site has shifted, rotated or reoriented relative to other patient tissues or structures following collection of the pre-operative data. Whichever method is used to align the pre-operative image with the real-time visualization, the ultimate authority to modify the image and to lock the alignment in place rests in the hands of the surgeon in control of the procedure.

Figure 9:
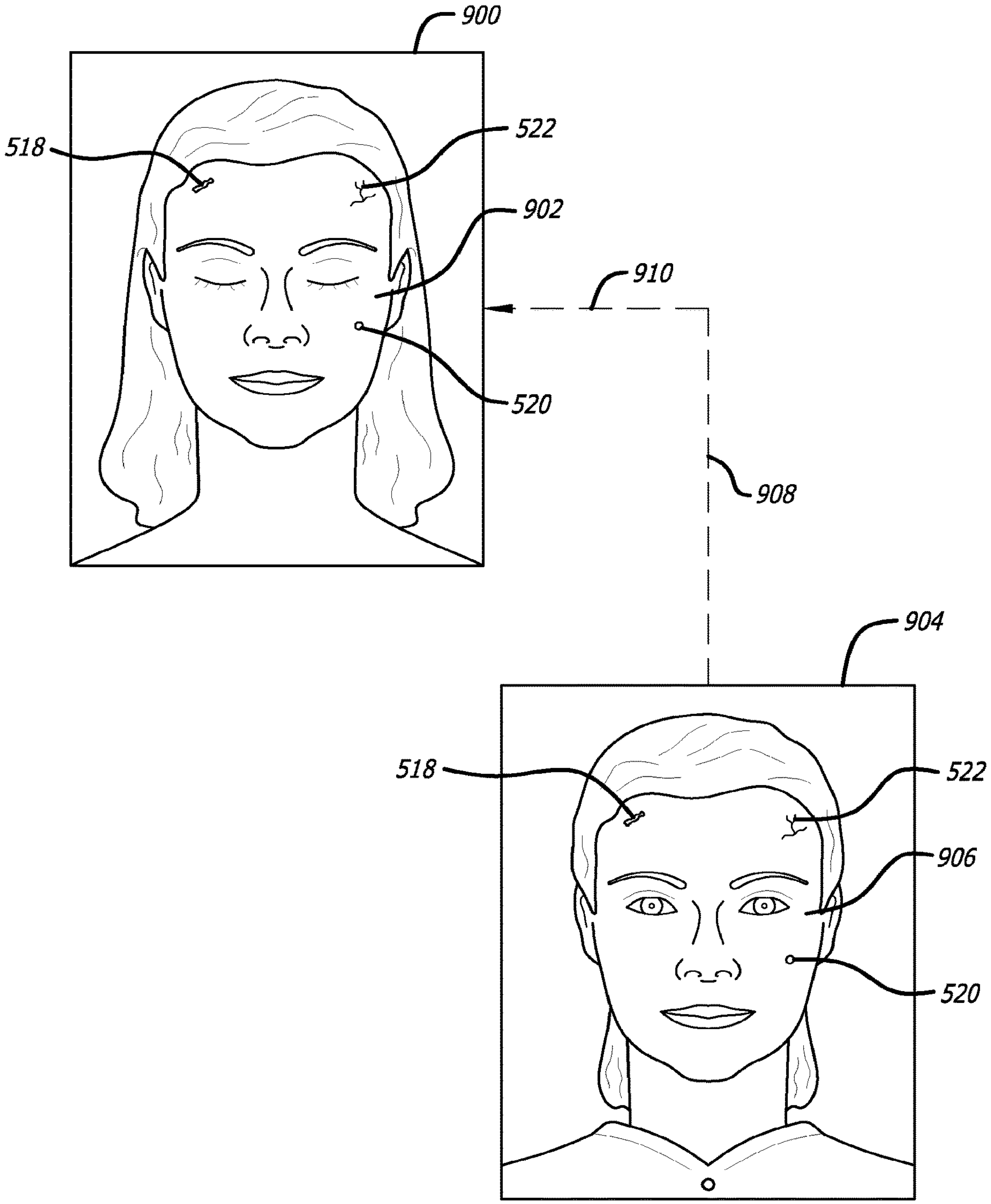
FIG. 9 is a front view of a patient illustrating an exemplary embodiment of a real-time 3D HD visualization overlaid with an aligned HD pre-operative patient data still image of the patient.

An exemplary pre-operative still image of the patient's eye is overlaid on one or more real-time 3D HD visualizations of at least a portion of the patient's target surgical site for at least a portion of the surgical procedure. Referring to FIG. 9, exemplary real-time 3D HD visualization 900 of a patient's face 902 on the operating table already under anesthesia is overlaid with pre-operative patient data still image 904 of the patient's face 906. Previously identified and recognizable fixed anatomical features including scar 518, mole 520 and vasculature 522 are used to align pre-operative patient data still image 904 with real-time 3D HD visualization 900.

It should be noted that pre-operative patient data still image 904 is shown as needing to be moved upward 908 and left 910 relative to real-time 3D HD visualization 900, for example by a surgeon, to achieve proper alignment. This alignment step can be performed manually by the surgeon or automatically by the at least one data processor and verified by the surgeon.

In an optional fourth calibration step, the controlling surgeon places a calibration target having known dimensions and features into the real-time multidimensional visualization of the target optical field of view within the target surgical site and triggers the apparatus to calibrate the target surgical site into consistent and useful measurable dimensions. The measurable dimensions may be in two or three dimensions and may enable quantitative digital measurement of linear, planar, or volumetric objects. It is within the scope of the present disclosure that this optional calibration step may be performed at any point in time, for example, pre-operatively, In a further step, the at least one data processor incorporates at least one real-time, virtual surgical guide or multiple surgical guides already established relative to the pre-operative still image into the real-time visualization of the target surgical site. It is to be noted that even if at least one virtual surgical guide had not been previously established, the surgeon is free to add them at this time either by the freehand method or by adding a template. Further, still, the surgeon can add at least one additional virtual surgical guide or delete one or more from the real-time visualization. It is within the scope of the present description that the virtual surgical guides may be incorporated at any point up until the guides are needed during a surgical procedure. Further, the virtual surgical guides can be added to the real-time visualization and removed any number of times at any point during the surgical procedure.

It should also be noted that when desired to correspond to a real-time 3D HD visualization of the target surgical site, the real-time virtual surgical guides can be generated in 3D as well as in HD, or both, depending on the particular surgical procedure or upon the needs of the surgeon. In some embodiments, either the real-time virtual surgical guides can be in 3D and/or HD and vice versa.

Figure 10:
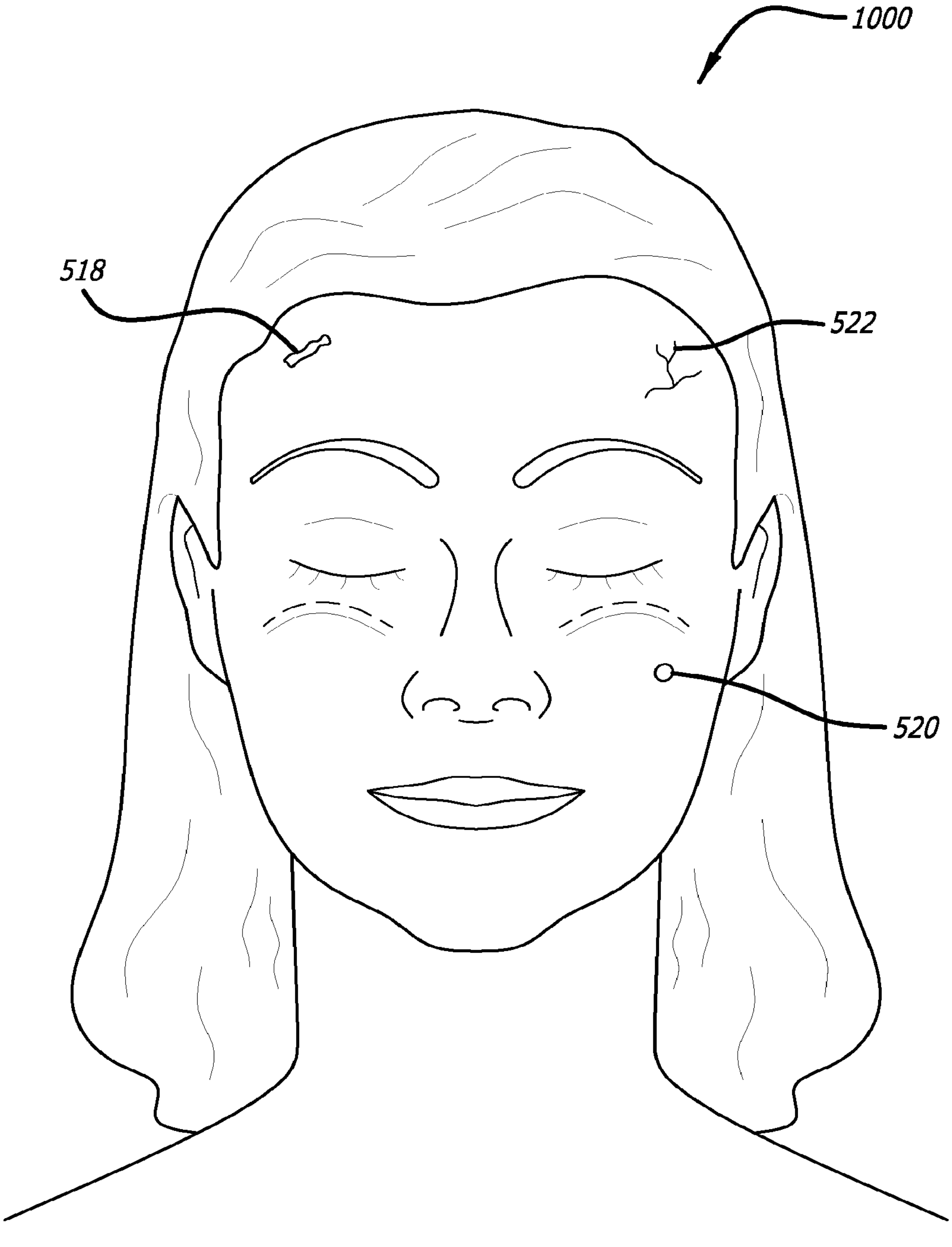
FIG. 10 is a front view of a patient illustrating an exemplary embodiment of a real-time visualization including virtual surgical guides.

At this point, after at least one virtual surgical guide has been added to the real-time visualization of the target surgical field, the surgeon may progress through the surgical procedure or portion thereof. As illustrated in FIG. 10, real-time 3D HD visualization 1000 of the target surgical site just after completion of a face lift and cheek implants incorporates the real-time, virtual surgical guides. As shown in FIG. 10, the eyebrows were lifted to the point of above first eye guide 506 and second above eye guide 510, and the cheek implants lifted the cheeks up to about sub eye guide 504 and second sub eye guide 508. Using these virtual surgical guides enables a surgeon to accurately and precisely perform a cosmetic or reconstructive surgery and attain desired symmetry of the new or moved features relative to one another and to the patient's face in general.

In another example according to the present invention, the apparatus and methods of the present invention can be utilized in breast reconstruction procedures. For example, after a man or woman is diagnosed with breast cancer, in some cases, one or both breasts must be removed. After removal of, for example, a single breast, often times particularly in the case of a woman, she will want the breast replaced. This type of reconstructive procedure is quite common. However, the problem with only constructing a single breast is that it needs to resemble, as closely as possible, an already existing breast.

Similarly, in the case where both breasts need reconstruction (bilateral reconstruction), one of the two breasts needs to be reconstructed first. Subsequently, the second breast can be reconstructed to match the first breast. A common primary objective of bilateral reconstruction is attainment of symmetric breast anatomy.

Figure 11:
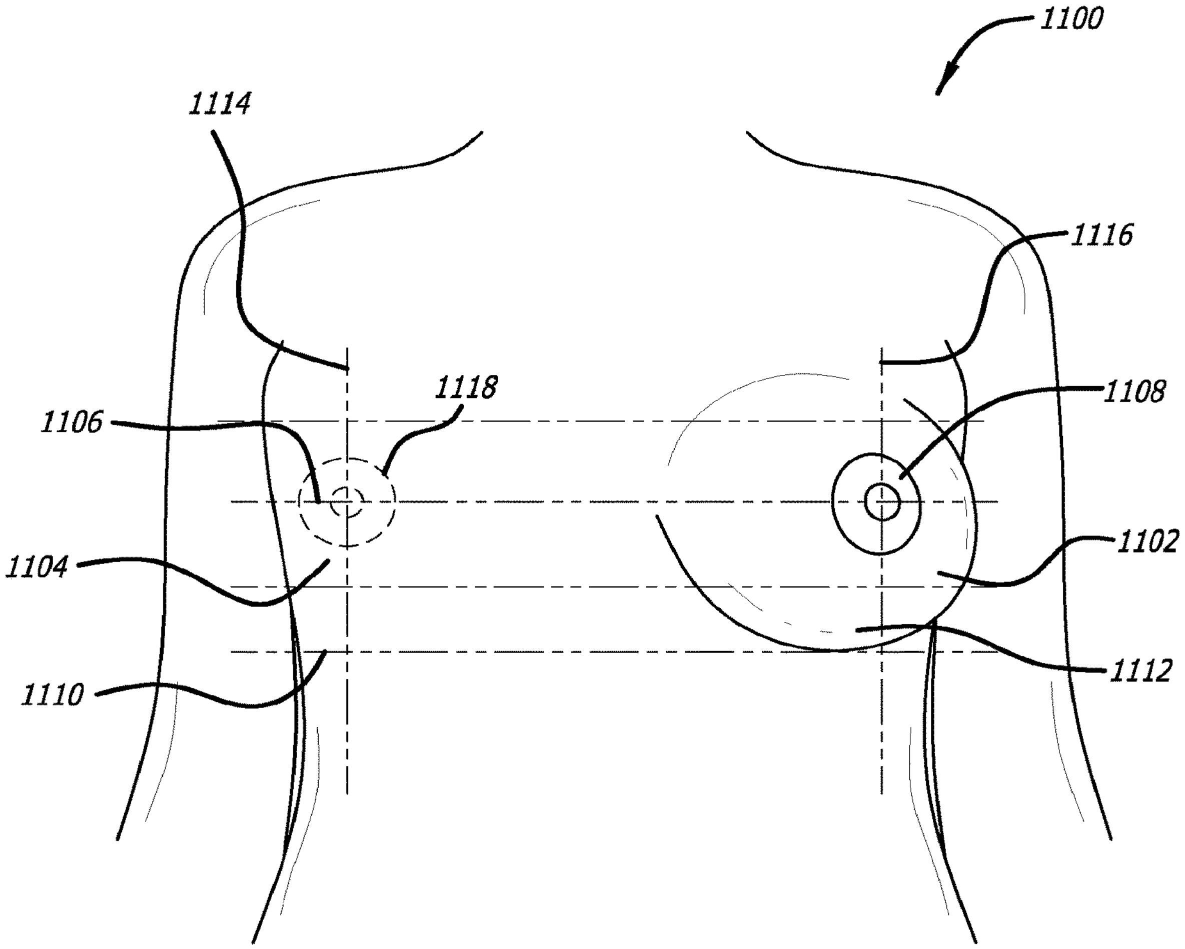
FIG. 11 is an illustration of a pre-operative still image of a patient's chest including virtual surgical guides.

Illustrated in FIG. 11, is pre-operative still image 1100 of a woman with original breast 1102 and surgically removed breast 1104. A goal of the surgeon is to implant and structure a new breast in the location of surgically removed breast 1104 that as closely as possible symmetrically matches original breast 1102. As such, the surgeon might add horizontal nipple line 1106 which will help locate a new nipple with original nipple 1108. Further, second horizontal line 1110 can be added to accurately gauge where the bottom of the new breast will be in relation to bottom 1112 of original breast 1102. Even further, first vertical line 1114 and second vertical line 1116 can be added to guide the surgeon horizontally during the procedure. To further aid the surgeon in proper nipple placement on the new breast, virtual nipple guide 1118 can be added and positioned accordingly. It is to be understood by those skilled in the art that virtual nipple guide 1118 can be generated directly from original nipple 1108, for example, using density recognition software to generate the guide.

Figure 12A:
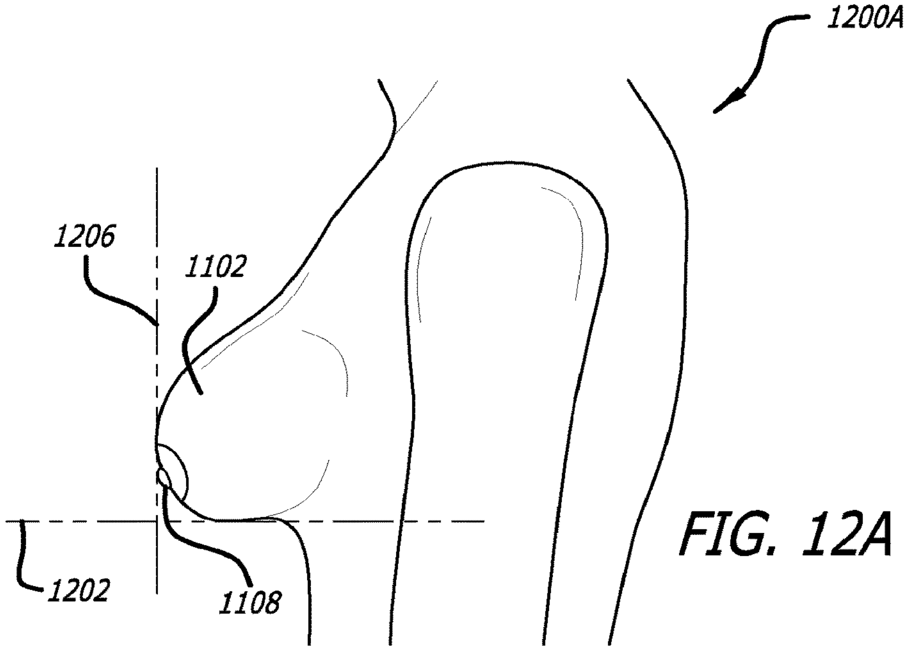
FIGS. 12A and 12B are illustrations of pre-operative still images of a patient's chest including virtual surgical guides.
Figure 12B:
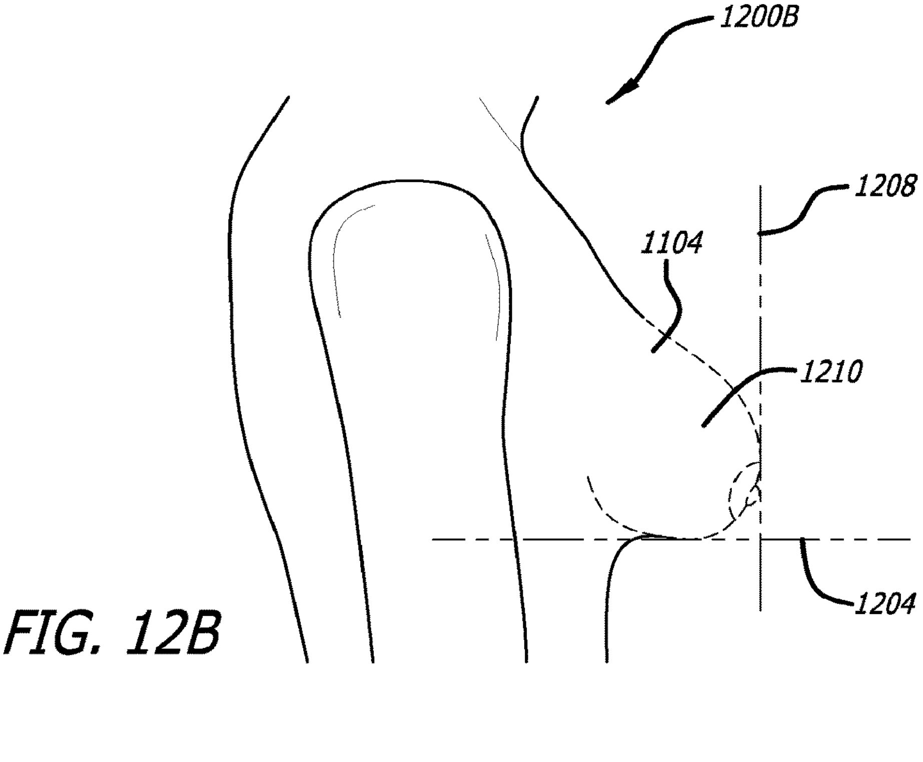

FIGS. 12A and 12B illustrate second side perspective pre-operative still images 1200A and 1200B of the woman in FIG. 11 with original breast 1102 and surgically removed breast 1104. In these still images, bottom guides 1202, 1204 are used to aid the surgeon in how low the new breast should extend to match original breast 1102. Additionally, front guides 1206, 1208 are used to aid the surgeon in how far extended from the chest the new breast should protrude to match original breast 1102. Even further, new breast guide 1210 can be used by the surgeon to match the new breast to original breast 1102.

Figure 13A:
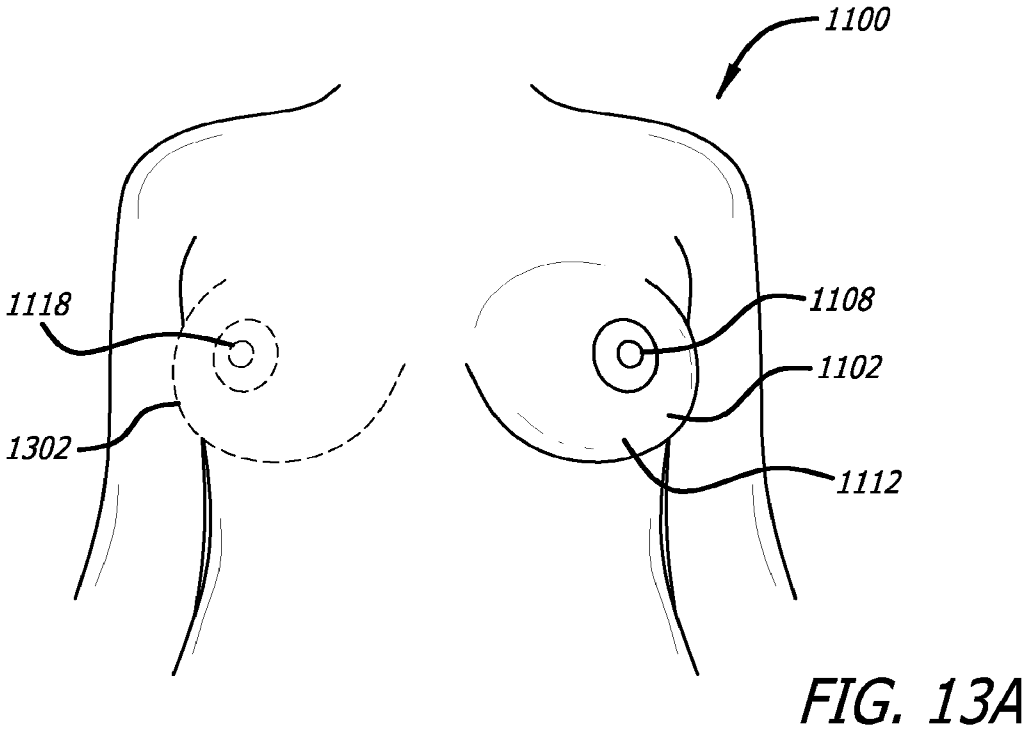
FIGS. 13A and 13B are illustrations of an alternative overlay of graphical information on a patient's chest including virtual surgical guides (FIG. 13A) and topographic contours (FIG. 13B).

As illustrated in FIG. 13A, in the absence of a breast guide, the system can use the features of original breast 1102 to overlay mirror image breast guide 1302 into the multidimensional visualization. Mirror image breast guide 1302 allows for proper alignment and scaling of the breast that is to be formed in relation to original breast 1102, which can provide reconstructive guidance to the surgeon. Further, mirror image breast guide 1302 can include features of other guides described such as, but not limited to virtual nipple guide 1118.

In one embodiment according to the present invention, a pre-operative image of a patient's chest region prior to a mastectomy is acquired. The pre-mastectomy image can then be overlaid onto the multidimensional visualization during the surgical procedure, such that the breast reconstruction can be most closely matched to the original pre-surgical anatomy.

Figure 13B:
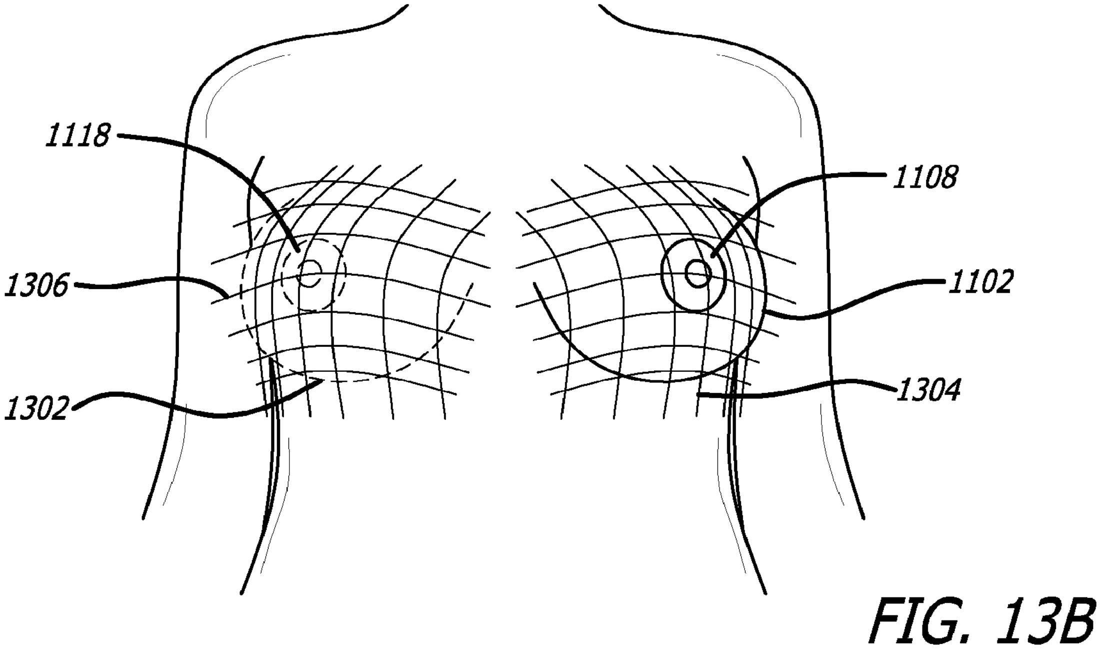

In a further embodiment of the device the system may use the three dimensional image overlay and real-time calibrated optical measurements to create a topographical map of the breast. FIG. 13B illustrates original breast 1102 overlaid with topographical map 1304 of the elevations of the breast. Topographical map 1304 can be mirrored to the opposite breast thereby creating mirrored topographical map 1306 and used with or without mirror image breast guide 1302 (or any other guide or template), or it can be used at the same location it was generated from.

Further, the topographical data between pre-operative and intra-operative images may be subtracted to create a pseudo thermal map which uses pseudo colors to represent different surface depths or protrusions (referenced to the still data). The still data may originate from a pre-operative image and analysis of the same surgical site or it may originate from an intra-operative image capture and analysis of the mirrored anatomy.

Figure 14:
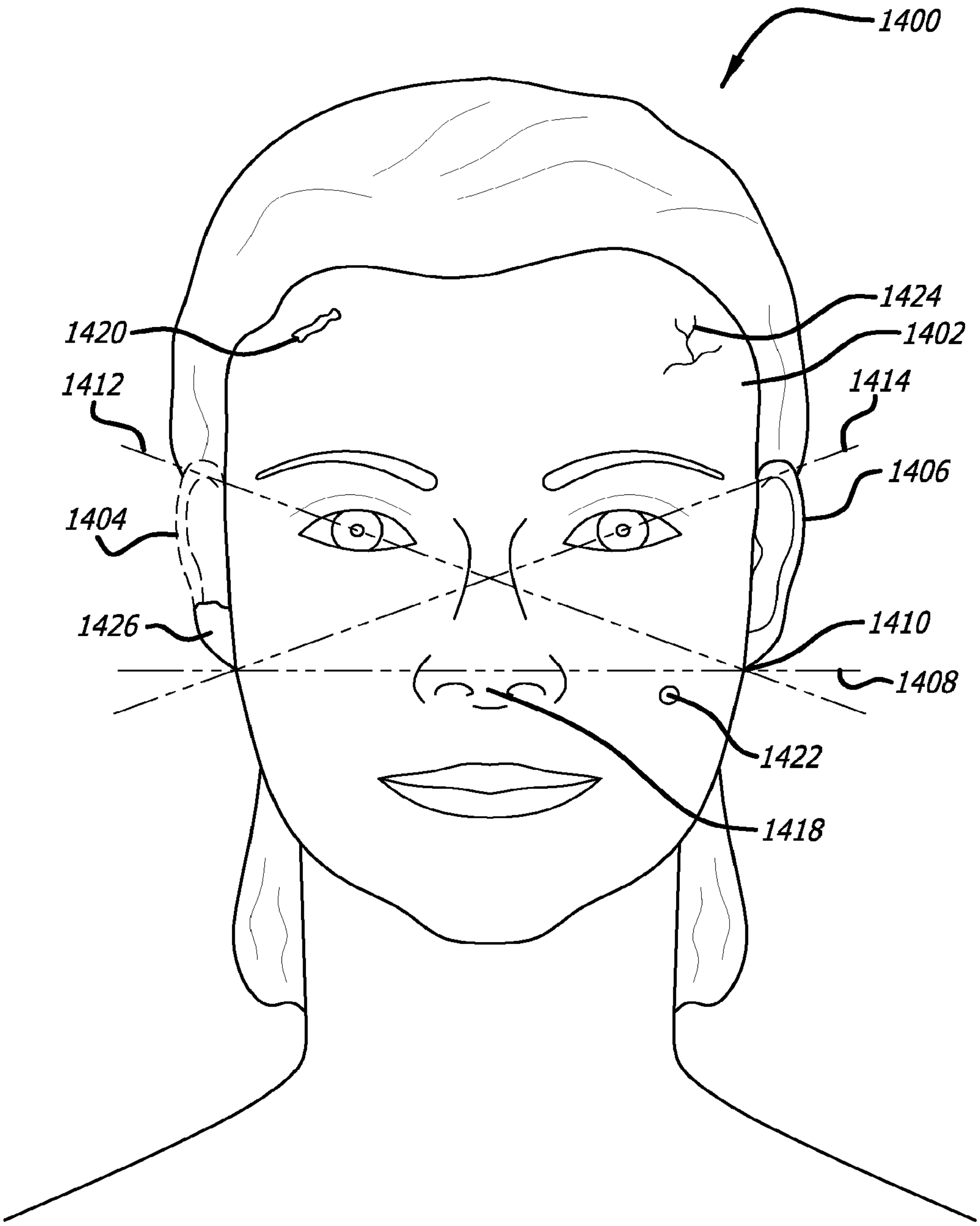
FIG. 14 is an illustration of a pre-operative still image including virtual surgical guides and fixed anatomical features.

In another exemplary embodiment according to the present invention, the apparatus and methods can be used to reconstruct an ear while keeping the shape, size and proportions precisely similar to the opposing ear. For example, FIG. 14 illustrates pre-operative still image 1400 of patent 1402 missing the lower half of her right ear 1404. Left ear 1406 is used as a guide to fabricate an accurate right ear. To do this, virtual surgical guide 1408 is added to align the future bottom of right ear 1404 with the bottom 1410 of left ear 1406. In order to assure proper facial symmetry, first diagonal virtual surgical guide 1412 and second diagonal virtual surgical guide 1414 can be added to the pre-operative still image and intersect at center point 1416 over nose 1418. These two diagonal guides allow a surgeon to properly attain facial symmetry by aligning the future bottom of right ear 1404 with the overall symmetry of the patient's face relative to left ear 1406.

At this point, just as in other examples, fixed anatomical features are used to align the pre-operative still image with a real-time multidimensional visualization of the target surgical site. Again, for example, scar 1420, mole 1422 and vasculature 1424 can be used as the fixed anatomical features. Then, once the still image and the real-time multidimensional visualization are locked in alignment, the surgeon can add or remove the virtual surgical guides at his discretion, and the surgery can commence. The targeted outcome of the surgery is reconstructed lower right ear 1426 which is properly aligned with bottom 1410 of left ear 1406.

It should be noted that it is within the scope and teachings of the present disclosure that the virtual surgical guides can be sized and modified according to the needs of the surgeon. For example, the guides can be sized, rotated and moved horizontally, vertically, and in depth as needed by the surgeon.

Further, the virtual surgical guides can be composed of different types of indication markings and can be in HD. For example, without limitation, the markings can be monochromatic or colored, with varying levels of transparency, composed of thin or thick lines, dashed or solid lines, a series of different shapes and the like as is consistent with contemporary digital graphics technology. Further, the graphic presentation can be different within individual guides to more easily visualize the guides in different areas or to emphasize specific areas of interest.

A further advantage of the apparatus and methods described herein is that the virtual surgical guides can be custom tailored to a specific body part, surgical cut, particular shape and the like as needed by the surgeon.

A surgeon will find that the apparatus and methods disclosed herein provide many more advantages over existing technology. Firstly, the virtual surgical guides are not affected by the surgical procedure itself. Therefore, they remain as constant references even when the target tissues are subjected to fluids and wiping, and even when inflammation to the affected area distorts dimensions. More importantly, the virtual surgical guides of the present invention are precise, accurate and tissue and structure specific, rather than the approximations known in the art. Further, they can be changed, removed, and reinstated as needed to provide an added degree of control and flexibility to the performance of a surgical procedure. For example, a controlling surgeon can chose to vary the transparency or remove a virtual surgical guide altogether from a visualization to give a more clear view of underlying tissues or structural features and then can reinstate the guide to function as a template for an incision or for the orientation of an implantable medical device, e.g. breast implant, in the target tissue or structure.

Further provided are significant advantages to patient and physician comfort as well as to a surgeon's stamina. This is because the real-time visualizations of the apparatus and methods of the present invention allow the surgery to take place under ambient or low ambient light conditions without sacrificing complete and accurate visualization of the target surgical site or of the associated virtual surgical guides. These capacities can be ideal for a surgeon and surgical team working long hours. Working such long hours under bright lights that generate intense heat in order to visualize the target surgical site, as is commonly the case in many known surgical procedures, can result in previously unavoidable surgeon discomfort and fatigue. Additionally, it is not uncommon for a surgeon to be wearing several layers of clothing along with surgical barriers, including gloves, face barriers, goggles, hats, and overcoats, to name a few, during a given surgical procedure, further contributing to discomfort and fatigue.

As an additional benefit of the described apparatus and methods, the ambient or low ambient lighting conditions that now can be utilized without sacrificing visualization and control also reduce reflected glare and high contrast shadows in the surgical environment that, in the past, could confuse or possibly even overwhelm the vision of the surgeon. Prior to the present description, a related visual limitation in surgery was that a surgeon commonly required surgical team members or students to position themselves in certain areas in order to reduce shadows that they might cast on the target surgical site. This resulted in limiting their view of the surgery. The present description addresses this problem by reducing shadows and increasing visibility, especially of the target site.

Similarly, it is not uncommon for a surgeon to look away from a target surgical site in order to change or to move equipment, to take a mental break, or to communicate with a surgical team or students. Upon looking back onto the traditional target surgical site, the surgeon would have to wait briefly to allow his eyes to adjust to the normal high intensity lighting, causing delays in the procedure. The present apparatus and methods eliminate this problem under low ambient light conditions.

Even further still, the apparatus and methods described herein allow a surgical team to position themselves in the most appropriate location for the surgery, not necessarily where the shadows dictate. Moreover, the apparatus and methods provide an ideal environment for students to observe a procedure in comfortable ambient to low ambient light conditions, especially when used with multiple screens or with a large display such as a projection screen.

The use of ambient or low ambient light in medical or surgical processes and the resulting reduced heat and complexity in the operating room also adds to the comfort of a surgical patient and enhances the compliance of the patient with the needs of the surgeon. Patient comfort during a surgical procedure is very important, especially when the patient is under local anesthesia and is conscious. It is not uncommon for bright lights to be focused on at least a portion of a patient, typically on the target surgical site. Such lighting systems can get hot and make a patient uncomfortable. Patients who are uncomfortable commonly are more on edge, squirm and/or twitch, or are tense. These are not ideal situations for a patient undergoing surgery. Such scenarios can be problematic for a patient. The present apparatus and methods' low ambient light capabilities can simplify and shorten a medical procedure, provide enhanced patient comfort and compliance, and improve the medical procedure's outcome; all while providing the surgeon with enhanced visual control of the process.

As those skilled in the art will appreciate, many of these capabilities result from the capacity of the present apparatus and methods to work with light outside of the visible range. Exemplary still images and videos captured at one or more wavelengths of light outside the visible range can be wavelengths of light shorter or longer than wavelengths of visible light. Exemplary wavelengths of light within the scope and teachings of the present invention are those with wavelengths longer that those of visible light, specifically between about 700 nm and about 1400 nm. Exemplary wavelengths that are outside of the wavelengths of normal visible light within the scope of the present invention also include wavelengths of light that are shorter than the wavelengths of visible light. These include wavelengths in the ultraviolet range or "UV," x-rays and gamma rays ranging from about 400 nm or less. A person skilled in the art should be cautious when using wavelengths of light shorter than the visible spectrum because, although such wavelengths of light can be advantageous for certain medical procedures, such wavelengths can be damaging to tissues.

Unless otherwise indicated, all numbers expressing composition or specifications of hardware components, properties such as distance, timing or speed, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method for guiding a surgical reconstructive or cosmetic procedure on a patient using a computer having a data processor, comprising:

recording, via at least one photosensor during surgery on the patient, visual data of a portion of a target surgical site;

producing in real time during the surgery, using the data processor and the visual data, a first video stream that includes one or more real-time multidimensional visualizations of the portion of the target surgical site, the portion including a body part of the patient that is symmetric to an opposing body part, the one or more real-time multidimensional visualizations including a three-dimensional stereoscopic representation of the portion of the target surgical site at a frame rate of at least 25 frames per second;

receiving, by the data processor, pre-operative or intraoperative patient data of the opposing body part as a surgical reference for the body part;

creating, by the data processor, a digital template with at least one virtual surgical guide for the body part using the pre-operative or intraoperative patient data of the opposing body part, such that creating the digital template includes automatically extracting a position of an identifiable anatomical feature related to the opposing body part from the pre-operative or intraoperative patient data with the data processor;

overlaying, by the data processor, the digital template onto the first video stream to create a second video stream; and presenting, via a display, the second video stream that includes one or more real-time multidimensional visualizations with the overlaid digital template to provide intraoperative surgical guidance.

2. The method of claim 1, wherein the digital template is created with the at least one virtual surgical guide by:

receiving, by the data processor, at least one second virtual surgical guide provided with respect to the opposing body part from the pre-operative or intraoperative patient data;

determining, by the data processor, an axis of symmetry of the patient from the pre-operative or intraoperative patient data; and creating, by the data processor, the at least one virtual surgical guide as a mirror image of the at least one second virtual surgical guide around the axis of symmetry.

3. The method of claim 2, wherein the axis of symmetry includes at least one of a horizontal axis or a vertical axis.

4. The method of claim 2, wherein the body part includes an eye and the axis of symmetry includes at least one of an eye brow axis, an eye axis, a lip axis, and a forehead axis.

5. The method of claim 2, wherein the at least one second virtual surgical guide is drawn by a surgeon.

6. The method of claim 2, wherein the at least one second virtual surgical guide is received by:

analyzing, by the data processor, the pre-operative or intraoperative patient data to locate the opposing body part;

determining, by the data processor, a guideline with respect the opposing body part; and creating, by the data processor, the at least one second virtual surgical guide based on the determined guideline.

7. The method of claim 6, wherein the body part includes an eye and the guideline includes at least one of an eye brow axis, an eye axis, a lip axis, and a forehead axis.

8. The method of claim 6, wherein the body part includes a breast and the guideline includes at least one of a nipple vertical axis, a nipple horizontal axis, a top breast horizontal axis, and a bottom breast horizontal axis.

9. The method of claim 1, wherein the body part and the opposing body part include at least one of an ear, a breast, a tooth, a nostril, an arm, a shoulder, a leg, a hand, or an eye.

10. The method of claim 1, wherein the digital template is configured by the data processor such that the at least one virtual surgical guide provides for having at least one of (i) symmetry or a mirror image between the body part and the opposing body part and (ii) the body part being reconstructed to match in size and shape the opposing body part.

11. The method of claim 1, wherein the digital template is combined with the one or more real-time multidimensional visualizations of the portion of the target surgical site by:

identifying, by the data processor, the identifiable anatomical feature within the pre-operative or intraoperative patient data or receiving, by the data processor, an indication of the identifiable anatomical feature for inclusion within the digital template;

creating, by the data processor, a graphic representative of the identifiable anatomical feature;

adding, by the data processor, the graphic representative to the digital template;

identifying, by the data processor, the identifiable anatomical feature within the one or more real-time multidimensional visualizations; and aligning, by the data processor, the graphic representative of the identifiable anatomical feature within the digital template with the identified identifiable anatomical feature within the one or more real-time multidimensional visualizations causing the digital template to be aligned with the one or more real-time multidimensional visualizations.

12. The method of claim 11, wherein the identifiable anatomical feature includes at least one of vasculature, a vascular network, a vascular branching pattern, a mole, a scratch, hair, a hairline, a dimple, a skin blemish, a skin wrinkle, a skin fold, a skin protrusion, a skin deformity, a skin blotch, a scar, a bony process, a bony ridge, a bony feature, and combinations thereof.

13. The method of claim 1, wherein the one or more real-time multidimensional visualizations are presented in conjunction with the digital template on a display device.

14. A method for guiding a surgeon in a surgical reconstructive or cosmetic procedure on a patient using a computer having a data processor, comprising:

recording, via at least one photosensor during surgery on the patient, visual data of a portion of a target surgical site;

creating in real time during the surgery, using the data processor and the visual data, a first video stream that includes one or more real-time multidimensional visualizations based on the visual data of the portion of the target surgical site including a body part that is symmetric to an opposing body part, the one or more real-time multidimensional visualizations including a three-dimensional stereoscopic representation of the portion of the target surgical site at a frame rate of at least 25 frames per second;

receiving, by the data processor, image data of the target surgical site from at least one of a medical device or a server that stores the image data from a medical device;

receiving, by the data processor, image data of the opposing body part as a surgical reference for the body part;

creating, by the data processor, a digital template with at least one virtual surgical guide for the body part using the image data of the opposing body part, such that creating the digital template includes automatically extracting a position of an identifiable anatomical feature related to the opposing body part from the image data with the data processor; and overlaying, by the data processor, the digital template onto the first video stream to create a second video stream to provide intraoperative surgical guidance to the surgeon.

15. The method of claim 14, further comprising:

causing the one or more real-time multidimensional visualizations to be displayed on a display device in conjunction with the digital template.

16. The method of claim 14, wherein the image data comprises at least one still image.

17. The method of claim 14, wherein at least one of the digital template and the one or more real-time multidimensional visualizations is stereoscopic.

18. The method of claim 14, further comprising:

combining, by the data processor, the digital template with the one or more real-time multidimensional visualizations by integrating, within a video signal, the digital template with the one or more real-time multidimensional visualizations.

19. The method of claim 14, further comprising:

causing, by the data processor, the digital template to be displayed on a display device at a specified depth with respect to the one or more real-time multidimensional visualizations.

20. The method of claim 14, wherein the method is configured to guide a surgical reconstructive procedure or cosmetic procedure selected from the group consisting of breast augmentation, lipoplasty, eyelid surgery, rhinoplasty, abdominoplasty, botulinum toxin injections, facelift, cheek implantation, dermal filler injections, transdermal treatments, heat treatments, UV treatments, broken nose repair, broken finger repair, ear defect reconstruction, skin reconstruction, birth defect reconstruction, and cleft palate repair.

21. The method of claim 14, wherein the at least one virtual surgical guide includes at least one of a line, an arc, a point, a circle, an axis, a line/plane of symmetry, an area, a topographical contour map, a pictorial representation, a measurement, a dimension, a freehand marking, an alphanumeric marking, and boundaries of a volumetric zone.

22. The method of claim 14, the method further comprising:

detecting, by the data processor, movement of the identifiable anatomical feature of the opposing body part within the one or more real-time multidimensional visualizations;

determining, by the data processor, a difference in position between the identifiable anatomical feature within the one or more real-time multidimensional visualizations and the indication of the identifiable anatomical feature within the digital template; and adjusting, by the data processor, a position of the digital template with respect to the one or more real-time multidimensional visualizations based on the determined difference in position such that the indication of the identifiable anatomical feature within the digital template is aligned with the identifiable anatomical feature within the one or more real-time multidimensional visualizations.

23. The method of claim 14, wherein the digital template includes a topographical map of the opposing body part, the method further comprising:

determining, by the data processor, an elevational difference between the topographical map and at least one of the image data and the one or more real-time multidimensional visualizations of the portion of the target surgical site;

creating, by the data processor, a thermal map that is indicative of the determined elevational differences; and causing, by the data processor, the thermal map to be displayed on a display device.

24. The method of claim 23, wherein the display device is further caused, by the data processor, to display the thermal map in conjunction with the topographical map to provide an indication of a surface depth of the body part in relation to a surface depth of the opposing body part.

25. The method of claim 23, wherein the thermal map is color-coded to represent different surface depths or protrusions.

26. The method of claim 23, further comprising:

receiving, by the data processor, optical measurements of at least one of surface depths or protrusions of the opposing body part; and using, by the data processor, the optical measurements in the creation of the topographical map.

* * * * *